(12) United States Patent
Windum et al.

(10) Patent No.: US 11,164,668 B2
(45) Date of Patent: Nov. 2, 2021

(54) PEN-TYPE DRUG DELIVERY DEVICE WITH ELECTRONIC DISPLAY ON CLIP MEMBER

(71) Applicant: Novo Nordisk A/S, Bagsvaerd (DK)

(72) Inventors: Jesper Peter Windum, Hilleroed (DK); Christian Plambech, Soeborg (DK); Lars Peter Klitmose, Gentofte (DK); John Oestergaard Madsen, Roedovre (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/519,031

(22) PCT Filed: Oct. 22, 2015

(86) PCT No.: PCT/EP2015/074478
§ 371 (c)(1),
(2) Date: Apr. 13, 2017

(87) PCT Pub. No.: WO2016/062807
PCT Pub. Date: Apr. 28, 2016

(65) Prior Publication Data
US 2017/0224927 A1    Aug. 10, 2017

(30) Foreign Application Priority Data
Oct. 23, 2014    (EP) .................................... 14190135

(51) Int. Cl.
*A61M 5/31*     (2006.01)
*G16H 20/17*    (2018.01)
(Continued)

(52) U.S. Cl.
CPC .............. *G16H 20/17* (2018.01); *A61M 5/20* (2013.01); *A61M 5/2033* (2013.01); *A61M 5/24* (2013.01);
(Continued)

(58) Field of Classification Search
CPC .......... A61M 5/31568; A61M 5/31533; A61M 5/31553; A61M 2005/3126
See application file for complete search history.

(56) References Cited

U.S. PATENT DOCUMENTS 4,654,631 A * 3/1987 Kurcbart ................... A45F 5/02
                                                     224/269
5,117,460 A * 5/1992 Berry ...................... G10L 15/00
                                                     340/7.39
(Continued)

FOREIGN PATENT DOCUMENTS

| CN | 103702699 | 4/2014 |
| CN | 104203315 B | 7/2017 |

(Continued)

*Primary Examiner* — Theodore J Stigell
*Assistant Examiner* — Courtney B Fredrickson
(74) *Attorney, Agent, or Firm* — Wesley Nicolas

(57) ABSTRACT

A portable pen-type drug injection device (300) comprises a main portion (301) and a clip (360). The clip comprises a base portion mounted to a portion of the drug delivery device, and a clip gripping portion with a free end. The device further comprises drug expelling means having dose setting means (340) allowing a user to set a dose of drug to be expelled, and a piston rod adapted to move a piston of a loaded cartridge in a distal direction to thereby expel drug from the cartridge. Electronic circuitry comprises sensor means adapted to detect a set and/or an expelled dose, and a display (374) is provided to display dose-related values, wherein at least a portion of the display is arranged in the flexible clip main portion.

14 Claims, 3 Drawing Sheets

(51) Int. Cl.
*A61M 5/24* (2006.01)
*A61M 5/315* (2006.01)
*A61M 5/20* (2006.01)
*A61M 5/32* (2006.01)

(52) U.S. Cl.
CPC ...... *A61M 5/3158* (2013.01); *A61M 5/31553* (2013.01); *A61M 5/31568* (2013.01); *A61M 5/31593* (2013.01); *A61M 5/3202* (2013.01); A61M 5/31535 (2013.01); A61M 2005/202 (2013.01); A61M 2005/2407 (2013.01); A61M 2005/3126 (2013.01); A61M 2205/50 (2013.01); A61M 2205/502 (2013.01); A61M 2205/52 (2013.01); A61M 2205/8206 (2013.01); A61M 2209/084 (2013.01)

(56) References Cited

U.S. PATENT DOCUMENTS

| | | | |
|---|---|---|---|
| 5,536,249 | A | 7/1996 | Castellano et al. |
| 5,593,390 | A * | 1/1997 | Castellano ........ A61M 5/31553 604/187 |
| 5,845,985 | A | 12/1998 | Xiong et al. |
| 6,585,698 | B1 * | 7/2003 | Packman ................ A61M 5/24 604/207 |
| 6,702,499 | B1 | 3/2004 | Fang |
| 7,008,399 | B2 | 3/2006 | Larsen et al. |
| 7,220,012 | B2 | 5/2007 | Liu |
| 9,623,188 | B2 | 4/2017 | Nielsen et al. |
| 9,782,543 | B2 | 10/2017 | Groeschke et al. |
| 10,376,644 | B2 | 8/2019 | Krusell et al. |
| 2003/0141325 | A1 * | 7/2003 | Balogh, II ................ A45F 5/00 224/101 |
| 2007/0017506 | A1 | 1/2007 | Bell et al. |
| 2009/0318865 | A1 | 12/2009 | Moller et al. |
| 2010/0286612 | A1 | 11/2010 | Cirillo et al. |
| 2012/0053527 | A1 | 3/2012 | Cirillo et al. |
| 2012/0232520 | A1 * | 9/2012 | Sloan ................ A61B 5/14532 604/504 |
| 2014/0018733 | A1 * | 1/2014 | Sjolund ................ A61J 7/0472 604/111 |
| 2014/0094743 | A1 | 4/2014 | Bengtsson |
| 2014/0099153 | A1 | 4/2014 | Pemberton-Pigott |
| 2014/0200545 | A1 * | 7/2014 | Bengtsson ............... A61M 5/24 604/506 |
| 2014/0207080 | A1 * | 7/2014 | Allerdings ............... A61M 5/24 604/207 |

FOREIGN PATENT DOCUMENTS

| | | | |
|---|---|---|---|
| CN | 105102023 B | 5/2019 | |
| EP | 0777123 A2 | 6/1997 | |
| EP | 2060284 A1 | 5/2009 | |
| JP | S5915591 | 1/1984 | |
| JP | S59143790 U | 9/1984 | |
| WO | 2006045525 A1 | 5/2006 | |
| WO | 2010052275 A2 | 5/2010 | |
| WO | WO-2012001493 A2 * | 1/2012 | ............ A61J 7/0472 |
| WO | WO-2012152628 A1 * | 11/2012 | .............. A61M 5/24 |
| WO | 2013004844 A1 | 1/2013 | |
| WO | WO-2013034716 A1 * | 3/2013 | .............. A61M 5/24 |
| WO | 2013120774 A1 | 8/2013 | |
| WO | 2013120778 A1 | 8/2013 | |

* cited by examiner

PEN-TYPE DRUG DELIVERY DEVICE WITH ELECTRONIC DISPLAY ON CLIP MEMBER

CROSS-REFERENCE TO RELATED APPLICATIONS

This application is a 35 U.S.C. § 371 National Stage application of International Application PCT/EP2015/074478 (published as WO 2016/062807), filed Oct. 22, 2015, which claims priority to European Patent Application 14190135.5, filed Oct. 23, 2014; the contents of which are incorporated herein by reference.

The present invention relates to portable drug devices comprising an electronic display. Especially, the invention relates to such devices adapted to capture and display data related to drug delivery.

BACKGROUND OF THE INVENTION

In the disclosure of the present invention reference is mostly made to devices to be used in the treatment of diabetes by delivery of insulin, however, this is only an exemplary use of the present invention.

Drug injection devices have greatly improved the lives of patients who must self-administer drugs and biological agents. Drug injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Thus, a number of injection devices comprising a dose monitoring/acquisition feature including a display to read out stored content have been suggested. For example, U.S. 2009/0318865 discloses a drug delivery pen with a display arranged on the pen body, this allowing a relatively large display to be utilized. EP 0 777 123 discloses a pen-formed drug delivery device in which a display is arranged on the clip base portion. In an alternative configuration WO 2010/052275 and U.S. Pat. No. 7,008,399 disclose drug delivery pens with a generally circular display arranged in the proximally facing end of the device with at least a portion of the corresponding electronics arranged in the axially moveable release button. However, with this design the form and size of the display is determined by the given size and form of the pen release button.

Having regard to the above, it is an object of the present invention to provide a portable drug delivery device comprising an electronic display which safely and reliably allows drug delivery data to be communicated to a user in a convenient way. The display and associated electronics should allow for a high degree of freedom of design for the drug delivery device and should be cost-effective in manufacturing.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a portable drug delivery device is provided comprising a device main portion with a clip, the clip comprising a base portion mounted to a portion of the drug delivery device, and a clip main portion with a free end. The device comprises a drug-filled cartridge or means for receiving a drug-filled cartridge, the cartridge comprising an axially displaceable piston and a distal outlet portion. The device is further provided with drug expelling means comprising dose setting means allowing a user to set the size of a dose of drug to be expelled, and a piston rod adapted to move the piston of a cartridge in a distal direction to thereby expel drug from the cartridge, as well as electronic circuitry comprising sensor means adapted to detect an event related to setting and/or expelling a dose of drug. The device further comprises a display adapted to display dose-related values, at least a portion of the display being arranged in the clip main portion. The term "mounted to" also covers embodiments in which the base portion is formed integrally with a portion of the drug delivery device, e.g. a housing component.

By incorporating the display in the clip main part, i.e. the gripping portion, a larger display can be provided without the necessity to integrate the display into the drug delivery device per se, this allowing a more compact, e.g. slimmer and/or shorter, design of the drug delivery device.

In addition to the display arranged at least partly in the clip gripping part electronic or electric components may be arranged in the clip base portion, the electronic or electric circuitry comprising e.g. an energy source and/or a processor. Smaller components may also be arranged in the clip gripping part, e.g. an antenna.

The clip may be mounted to the device main portion or to a cap releasably mountable to the device main portion, the cap being adapted to enclose the outlet portion of a mounted cartridge.

In case the clip is mounted to the device main portion the sensor means may be adapted to detect the size of a set and/or an expelled dose.

In case the clip is mounted to the cap the electronic circuitry may be arranged in the cap with the sensor means adapted to detect a cap event, e.g. cap-on or cap-off, the electronic circuitry being adapted to create a time-stamp when a cap event is detected, and the display being adapted to display a time parameter related to a cap event. Alternatively, the sensor means may be arranged in the device main portion and adapted to detect the size of a set and/or an expelled dose, the drug delivery device comprising means allowing electric power and/or data, e.g. wirelessly, to be exchanged between the cap-mounted clip and the device main portion.

The clip gripping part may be flexible and the display may be flexible as well, e.g. comprising no breakable glass components. The latter will also allow the display to be curved. The display may be an LCD, OLED display, printed display or E-ink display adapted to display numeric values. The display may be laminated to a cover member. In exemplary embodiments a flexible clip main portion is configured to allow the free end to elastically move at least 1 mm away from the surface to which the clip base portion is mounted.

In an alternative configuration the clip gripping portion may be "stiff" and the clip holding action may be provided by a distally mounted "pinch" member, e.g. a flexible member or a spring-biased member. By this design a traditional "stiff" glass display may be used. As a further alternative a stiff clip gripping portion may be attached to the clip base by a hinge, the hinge providing a pinching force.

Although the term "clip" in the present context is considered to be a well-known technical term to the skilled person, the above-mentioned clip main portion may be defined as having an elongate configuration with a length defined between its free end and the attachment to the base portion, the clip main portion having a width smaller than the length. The clip main portion is arranged with a distance to the portion of the drug delivery device to which the base portion is mounted or formed integrally with, this forming a gap allowing e.g. a piece of clothing to be introduced into the gap.

In exemplary embodiments the electronic circuitry comprises logging means adapted to create a log for dose amounts of drug expelled from a cartridge by the drug expelling means.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. The drug may be a single drug compound or a premixed or co-formulated multiple drug compounds drug agent from a single reservoir. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin and GLP-1 containing drugs, this including analogues thereof as well as combinations with one or more other drugs.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Figure 1:
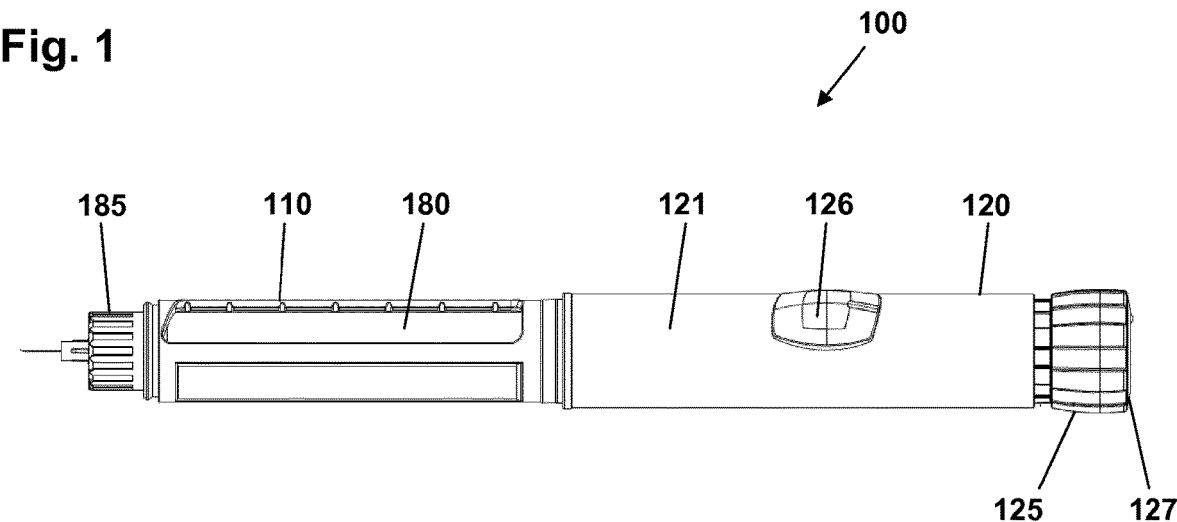
FIG. 1 shows a pen-formed drug delivery device with an end-mounted display.

Referring to FIG. 1 a pen-formed drug delivery device as disclosed in WO 2010/052275 will be described. In the present context the device represents a "generic" prior art drug delivery device providing an example of a device provided with dose detecting means and a generally round proximal end-mounted display for displaying information related to detected dose sizes. A drug delivery device similar to the device of FIG. 1 is marketed by Novo Nordisk as NovoPen Echo®.

More specifically, the pen device 100 comprises a cap part (not shown) and a main part having a proximal body or drive assembly portion 120 with a housing 121 in which a drug expelling mechanism is arranged or integrated, and a distal cartridge holder portion in which a drug-filled transparent cartridge 180 with a distal needle-penetrable septum can be arranged and retained in place by a cartridge holder 110 releasably attached to the proximal portion, e.g. by a threaded connection or a bayonet coupling, the cartridge holder having openings allowing a portion of the cartridge to be inspected. The cartridge may for example contain an insulin, GLP-1 or growth hormone formulation. The device is designed to be loaded by the user with a new cartridge through a proximal receiving opening in the cartridge holder, the cartridge being provided with a piston driven by a piston rod forming part of the expelling mechanism. A proximal-most rotatable dose member 125 serves to manually set a desired dose of drug shown in display window 126 and which can then be expelled when the button 127 is actuated. Depending on the type of expelling mechanism embodied in a given drug delivery device, the expelling mechanism may comprise a spring which is strained during dose setting and then released to drive the piston rod when the release button is actuated, this as known from e.g. the ServoPen® offered by Ypsomed. Alternatively the expelling mechanism may be fully manual in which case the dose member and the actuation button moves proximally during dose setting corresponding to the set dose size, and then is moved distally by the user to expel the set dose, this corresponding to the shown embodiment. The cartridge is provided with distal coupling means in the form of a needle hub mount allowing a needle assembly 185 to be mounted, e.g. by means of a thread or a bayonet coupling.

As appears, FIG. 1 shows a "rear-loaded" drug delivery device in which the cartridge holder adapted to be removed from the device main portion, however, the drug delivery device may alternatively be of the front-loaded type in which a cartridge is inserted through a distal opening in the cartridge holder which in non-removable attached to the main part of the device.

Figure 2A:
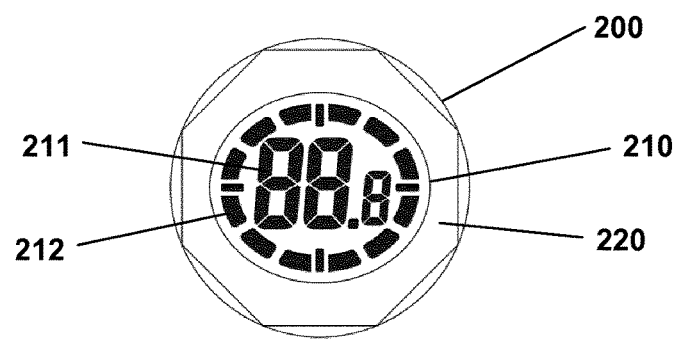
FIG. 2A shows in an end view the display of the FIG. 1 device.

The pen device of FIG. 1 comprises electronic circuitry allowing an expelled dose of drug to be registered and shown on a proximally facing display together with an indication of the time since the dose was expelled. Correspondingly, the device comprises a display in the form of liquid crystal display (LCD) as shown in FIG. 2A. The figure shows the LCD component 200 per se and as appears the effective display area 210 is somewhat smaller than the component itself. When mounted in the device the circumferential blank portion 220 is covered by a rim. The particular embodiment shown is designed to show dosage size and time elapsed since the last performed injection. The dosage size is shown numerically in units of insulin IU centrally in the display by 7-segment numbers 211 and the time since last injection is indicated as hours lapsed since the injection using peripherally arranged segments 212, the number of segments displayed providing a quick reference to the time elapsed since the last injection, e.g. each segment indicating that one hour has elapsed. In particular embodiments a plurality of previously stored expelled dosage sizes along with timing information are stored as data sets and may be shown on display 200 by sequentially operating the dosage selector 125, e.g. by axially moving the dosage selector back and forth or alternatively by rotating the dosage selector.

Figure 2B:
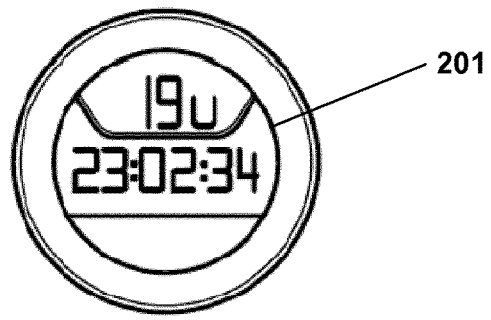
FIG. 2B shows in an alternative configuration for a display for the FIG. 1 device.

FIG. 2B shows an alternative configuration for a proximally mounted round display 201 having two lines for numeric values. The display can be configured to show data in different formats. For example, the display of FIG. 2B is a two-line display in which time is shown using a HH:MM:SS stop watch design, this providing that the time since the last dose expelled from the device can be shown with a running second counter allowing a user to easily identify the shown information as a counting time value. After 24 hours the display may continue to display time in the HH:MM:SS format or change to a day and hour format.

As a typical pen-formed drug delivery device typically has a general outer diameter in the 15-18 mm range, it follows that the size of the shown numerals and symbols are rather small and may thus be difficult to read for users with impaired vision, e.g. many elderly persons.

Figure 3:
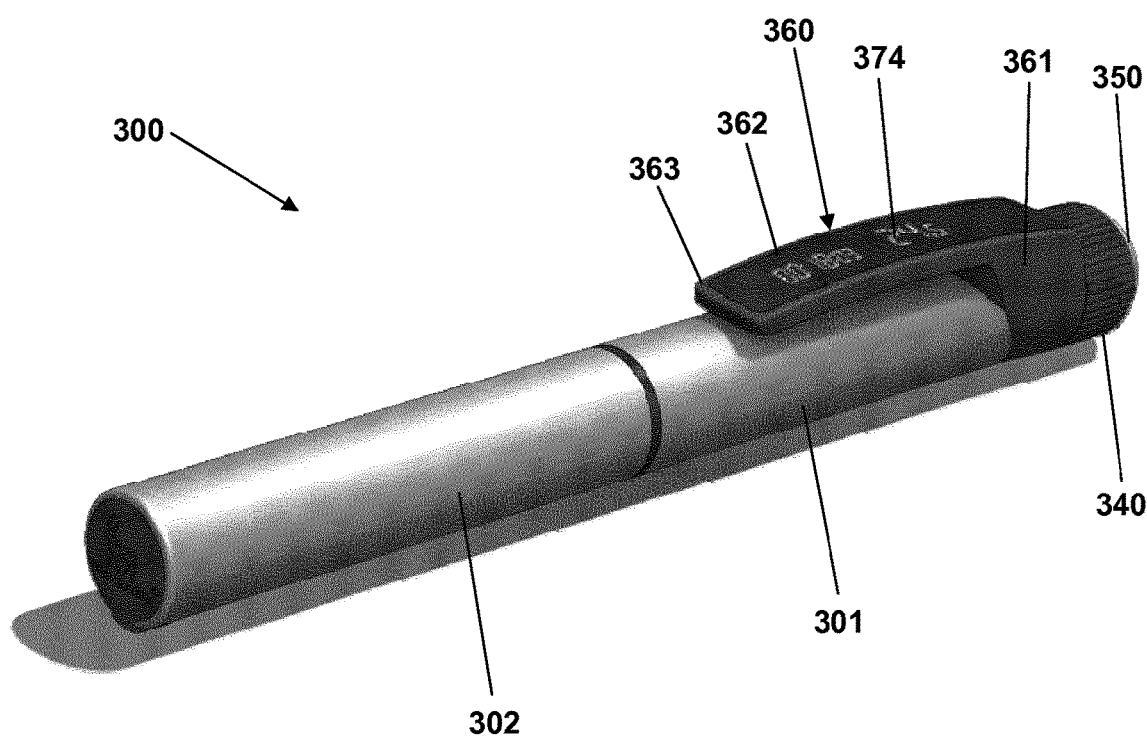
FIG. 3 shows a pen-formed drug delivery device with a display mounted in a clip.

Addressing this issue FIG. 3 shows a pen-formed drug delivery device 300 having a pocket clip 360 mounted to the pen main body 301 and not the cap 302. The clip 360 comprises a base portion 361 attached to the housing and a distally extending flexible portion 362 having a free distal end 363 allowing the clip to grip e.g. the edge of a shirt pocket. The clip comprises an electronic display 374 which in the shown embodiment is curved in the longitudinal direction corresponding to the curvature of the clip. The shown device comprises an expelling mechanism with a spring which is strained when the dose setting member 340 is rotated during dose setting, the set dose being released to drive the piston rod when the release button 350 is actuated. In the shown embodiment the display is designed to display the same information as the round display shown in FIG. 2B, i.e. dose size and time-since-last dose using a HH:MM:SS stop watch design. As is apparent the size of the numerals can be made larger. Further, by utilizing an existing structure for a further purpose components in the drug delivery device can be re-arranged to thereby achieve a more attractive and user-friendly design. More specifically, by moving the display and, depending on the design, further electronic components away from the main body a slimmer and/or shorter over-all design may be achieved. In the shown embodiment the side-way orientation of the display also allows the clip display to be used to show the actual dose size during dose setting, the display thereby replacing the mechanical dose setting display 126 of the FIG. 1 embodiment.

Figure 4:
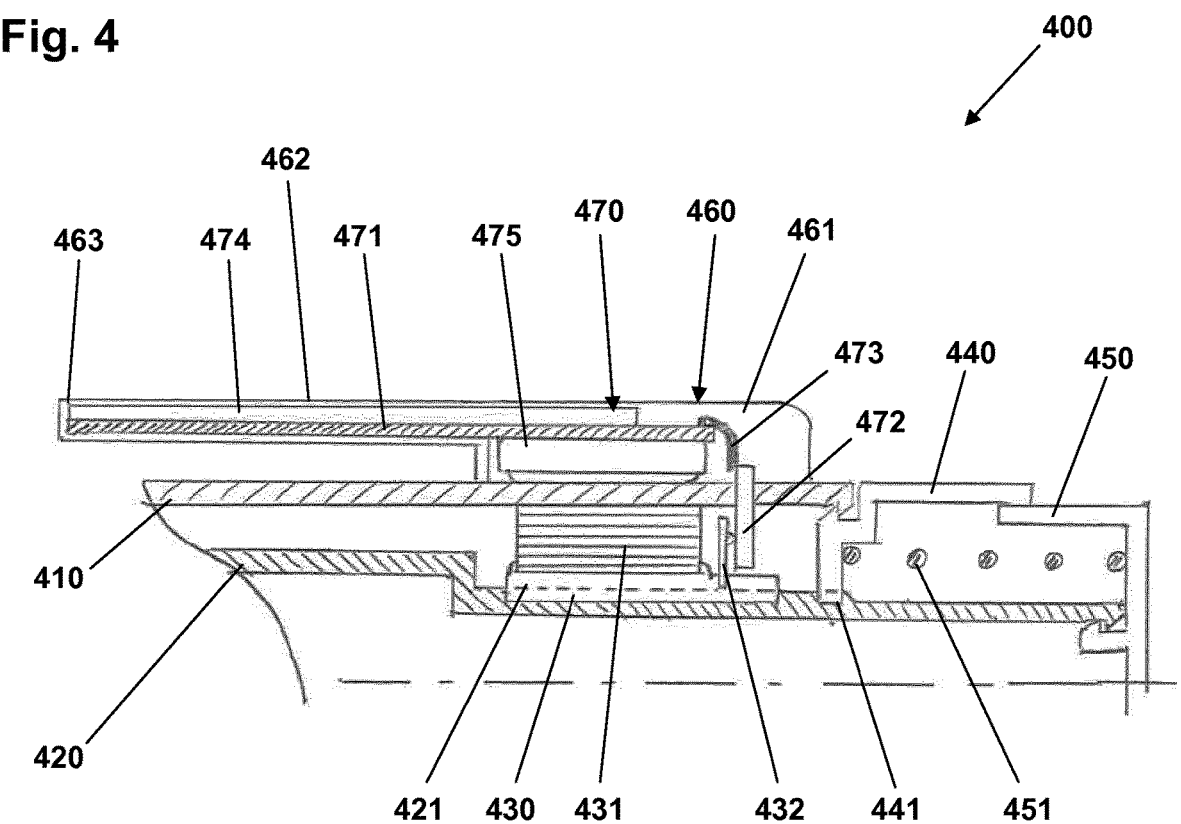
FIG. 4 shows a proximal portion of a drug delivery device incorporating a clip-mounted display.

In FIG. 4 a proximal portion of a drug delivery device incorporating a clip-mounted display is shown in a schematic representation. The figure shows how dose sensing means and a clip-mounted display can be incorporated in a drug delivery device of the spring-driven type.

More specifically the drug delivery device 400 comprises a generally tubular housing 410, a drive tube 420, a ring-formed spring and sensor mount member 430, a rotatable dose setting member 440, a proximal release button 450, a clip 460, and dose sensing electronic circuitry 470. The device further comprises a piston rod and a driver for rotating the piston rod to thereby move it distally (not shown). A scale drum (not shown) may provide a mechanical dose display. The mount member 430 is non-rotationally coupled to the drive tube 420 via a splined connection 421 allowing the drive tube to be moved axially relatively to the mount member which is arranged axially fixed relative to the housing. A spirally wound spring 431 is attached to the housing respectively the mount member, this allowing the spring to be strained as the mount member is rotated together with drive tube during dose setting. A ring-formed first rotary sensor part 432 is mounted to the mount member and rotates therewith. A corresponding stationary second ring-formed rotary sensor part 472 is mounted in the housing, the two sensor parts together forming a rotary sensor assembly which in combination with electronic circuitry provides a rotary encoder providing data that can be used to calculate dose size data. The rotating first rotary sensor part may be a "passive" metal member engaging corresponding coding structures on the stationary second rotary sensor part as the two rotary sensor parts rotate relative to each other. A more detailed description of rotary encoders can be found in PCT/EP2014/053221 which is hereby incorporated by reference.

The dose setting member 440 is arranged axially fixed relative to the housing and is coupled to the drive member via a splined connection 441 allowing the dose setting member to rotate the drive tube during dose setting. A releasable two-way ratchet mechanism (not shown) is arranged between the housing and the drive tube and provides that the drive member can be rotated to and held in a given rotational position with the spring being strained correspondingly, the two-way feature providing that a dose can be set and adjusted bi-directionally. A drive coupling (not shown) is arranged between the drive tube and the drive member, the drive coupling being dis-engaged during dose setting. A release button 450 is coupled to the drive tube, the release button being biased proximally by a spring 451.

The clip 460 comprises a base portion 461 attached to the housing and a distally extending flexible portion 462 having a free distal end 463 allowing the clip to grip e.g. the edge of a shirt pocket. The clip houses electronic circuitry 470 comprising a flexible PCB 471, a flexible display 474, and a "battery" 475. As shown the battery is mounted in the clip base portion and the PCB and display are mounted partially in the flexible free portion of the clip. The PCB is connected to the stationary second rotary sensor part 472 via a connector 473. Additional electronic components providing processor, transmitter-receiver, antenna as well as memory may be arranged in the clip base portion, the free clip portion or inside the housing depending on the specific design and the space requirements of the components, this allowing a high degree of freedom of design. Further, an axial dose switch (not shown) is provided and connected to the PCB, the switch detecting whether the device is in a dose-setting or out-dosing state.

During normal operation of the device the following takes place. The user sets a dose to be expelled by rotating the dose setting member to a desired rotational position correspond to a desired set dose, thereby straining the drive spring correspondingly. During dose setting the dose switch is in the dose setting state and the rotational movement is detected as a set dose, which may be shown on the display. When the user desires to expel the set dose the release button and thereby the drive tuber is moved distally whereby the following takes place: (i) the drive tube dis-engages the dose setting member corresponding to the splined connection 441, (ii) the drive tube engages the drive member via the drive coupling, and (iii) the drive tube is released from the dose setting ratchet mechanism, whereby the spring is released rotating the drive tube and drive member to thereby drive the piston rod distally to thereby expel a dose of drug from a loaded cartridge. As the drive tube is moved distally the dose switch is shifted from dose-setting mode to out-dosing mode and the rotational movement detected by the rotational encoder is correspondingly used to register and calculate the amount of drug expelled. When the set dose has been expelled (or the expelling action has been paused for a pre-set amount of time) the expelled dose size is shown in the display and the stop watch counter starts to run. After some seconds the display will time out but may be turned on again by e.g. depressing the release button.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A portable drug delivery device comprising:
a device main portion,
a permanently mounted clip comprising a base portion mounted to a portion of the drug delivery device, and a flexible clip main portion with a free end forming a gap between the drug delivery device and the clip main portion,
a drug-filled cartridge or structure for receiving a drug-filled cartridge, the cartridge comprising an axially displaceable piston and a distal outlet portion,
a drug expelling structure comprising:
a dose setting structure allowing a user to set the size of a dose of drug to be expelled, and
a piston rod adapted to move the piston of a cartridge in a distal direction to thereby expel drug from the cartridge, and
electronic circuitry comprising a sensor structure adapted to detect an event related to setting or expelling a dose of drug, and
a flexible display adapted to display a dose-related value, wherein at least a portion of the display is arranged on the free end of the flexible clip main portion, and the flexible display is configured to simultaneously display the dose-related values of dose size and time-since-last dose.

2. The drug delivery device as in claim 1, wherein at least a portion of the electronic circuitry is arranged in the clip base portion, the electronic circuitry comprising one or more of the following components: an energy source and a processor.

3. The drug delivery device as in claim 1, wherein the clip is mounted to the device main portion.

4. The drug delivery device as in claim 1, wherein the sensor structure is adapted to detect the size of a set and/or an expelled dose.

5. The drug delivery device as in claim 1, further comprising a cap releasably mountable to the device main portion to enclose the distal outlet portion of a mounted cartridge, the clip being mounted to the cap.

6. The drug delivery device as in claim 5, wherein:
the electronic circuitry is arranged in the cap,
the sensor structure is adapted to detect a cap event,
the electronic circuitry is adapted to create a time-stamp when a cap event is detected, and
the display is adapted to display a time parameter related to a cap event.

7. The drug delivery device as in claim 5, wherein the sensor structure is arranged in the device main portion and adapted to detect the size of a set and/or an expelled dose, the drug delivery device comprising a structure allowing electric power and/or data to be exchanged between the cap and the device main portion.

8. The drug delivery device as in claim 1, wherein the display is curved.

9. The drug delivery device as in claim 1, wherein the display is an LCD, OLED display, printed display or E-ink display adapted to display numeric values.

10. The drug delivery device as in claim 1, wherein the electronic circuitry comprises a logging structure adapted to create a log for dose amounts of drug set and/or expelled from a cartridge by the drug expelling structure.

11. The drug delivery device as in claim 1, wherein the device main portion defines a main longitudinal axis, the clip main portion being flexible and having a longitudinal configuration and being arranged corresponding to the main longitudinal axis.

12. The drug delivery device as in claim 1, wherein the electronic circuitry comprises a printed circuit board (PCB), at least a portion of the PCB is arranged in the free end of the flexible clip main portion, and at least a portion of the PCB is arranged in the base portion.

13. The drug delivery device as in claim 1, wherein the electronic circuitry comprises a battery arranged in the clip base portion.

14. The drug delivery device as in claim 1, further comprising a cap releasably mountable to the device main portion to enclose the distal outlet portion of a mounted cartridge, wherein the clip base portion is mounted to the device main portion and not to the cap.

* * * * *